US00PP37393P2

(12) United States Plant Patent
Hansen

(10) Patent No.: US PP37,393 P2
(45) Date of Patent: Apr. 28, 2026

(54) ***ANDROPOGON* GRASS NAMED 'Blue Steel'**

(50) Latin Name: *Andropogon gracilis*
Varietal Denomination: Blue Steel

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,865

(22) Filed: Oct. 14, 2025

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

(56) References Cited

U.S. PATENT DOCUMENTS

PP16,162 P3 * 12/2005 Diboll ..... Plt./384

* cited by examiner

*Primary Examiner* — Susan McCormick Ewoldt
*Assistant Examiner* — Zachariah Allan Kay

(57) ABSTRACT

A new and distinct ornamental Big Bluestem Grass *Andropogon* plant named 'Blue Steel' with broad, distally-arching, bluish-green foliage that develops reddish-purple leaf ends about late summer. The upright and dense culms that resist lodging produce medium-height plants with panicles beginning purplish-grey and becoming tan seed heads that are retained into winter. The new plant is useful in the landscape as a specimen or en masse.

2 Drawing Sheets

Latin botanical classification: *Andropogon gracilis.*
Variety denomination: 'Blue Steel'.

STATEMENT REGARDING PRIOR DISCLOSURES UNDER 37 CFR 1.77(B)(6)

The first offer for sale was privately made to Prides Corner Farm and Overdevest Nurseries, L.P. by Walters Gardens, Inc. on Oct. 15, 2024. Walters Gardens, Inc. obtained the plant and all information relating thereto from the inventor. No plants of *Andropogon* 'Blue Steel' have been sold in this country or anywhere in the world. The offer for sale was within one year from the filing of this application.

BACKGROUND OF THE PLANT

*Andropogon* 'Blue Steel', hereinafter also referred to just by the cultivar name 'Blue Steel' and the "new plant" is a new and distinct cultivar of Big Bluestem Grass.

The new plant originated as a cross by the inventor of the proprietary unnamed hybrid referenced only by the breeder code '20-3-4' (not patented) with the proprietary unnamed hybrid referenced only by the breeder code 20-42-1 (not patented) at a wholesale perennial nursery in Zeeland, Michigan in the summer of 2021. The seed was collected in the autumn of 2021 and sown the following spring. The individual seedling was initially selected from among many for further observation in the summer and fall of 2021 at which time it was assigned the breeder code 21-17-17 before assigning the new plant a cultivar name.

The new plant has been successfully asexually propagated by division since late fall of 2022 at the same wholesale perennial plant nursery in Zeeland, MI, and found to produce stable and identical plants that maintain the unique characteristics of the original plant. The plant is stable and reproduces true-to-type in successive generations of asexual reproduction.

BRIEF SUMMARY OF THE PLANT

*Andropogon* 'Blue Steel' differs from the female parent and male parent in that the new plant is smaller and not as caespitose as either.

The nearest comparison varieties known to the inventor are: 'Big Daddy' U.S. Plant Pat. No. 16,162, 'Blackhawks' U.S. Plant Pat. No. 27,949, and 'Indian Warrior', U.S. Plant Pat. No. 24,999.

'Big Daddy' is significantly taller and broader in habit. 'Blackhawks' has a slightly taller more columnar and tighter rhizomatous habit and the foliage turns a more complete purplish-grey earlier in the season with more greyish-purple panicles. 'Indian Warrior' has a taller habit and the summer foliage is darker green and less bluish-green.

The new plant is shorter and more broadly rhizomatous than either of these known comparison cultivars.

The following traits of *Andropogon* 'Blue Steel', in combination, have been repeatedly observed in multiple generations of asexually propagated plants and distinguish the new plant from all other Big Bluestem Grass plants known to the inventor:

1. Broad bluish-green foliage that develops reddish-purple leaf ends in late summer;
2. Upright and dense culms producing medium height plants that do not lodge;
3. Foliage is upright and distally arching;
4. Panicles beginning purplish-grey and becoming tan seed heads that are retained into winter;
5. Develops into a broad rhizomatous clump.

BRIEF DESCRIPTION OF THE DRAWINGS

The photographs of the new plant demonstrate the overall appearance of a five-year-old plant growing in an outdoor display garden in Zeeland, MI, including the unique traits. The colors are as accurate as reasonably possible with color reproductions. Ambient light spectrum, source, and direction may cause the appearance of minor variation in color.

DETAILED BOTANICAL DESCRIPTION

Figure 1:
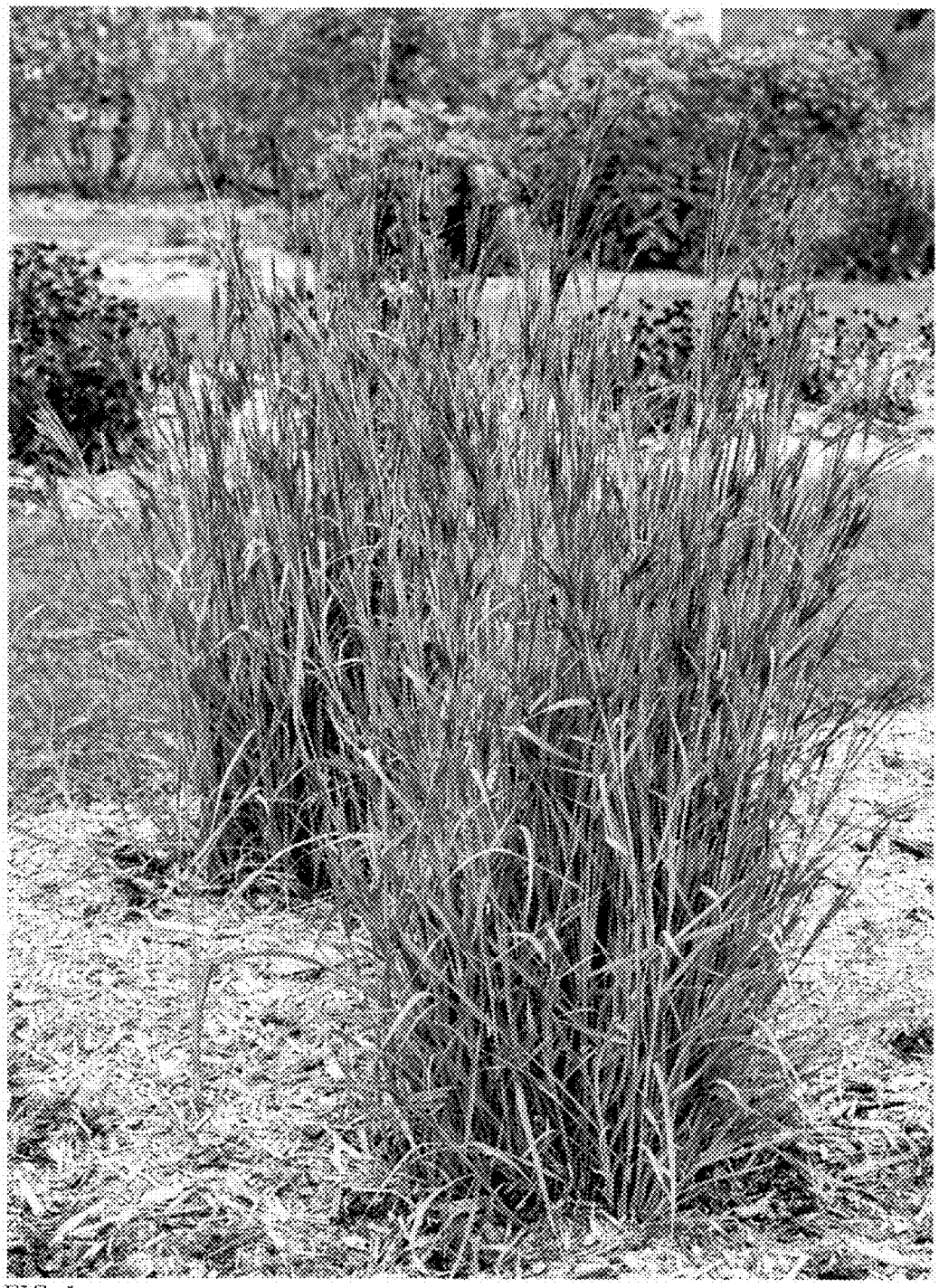
FIG. 1 shows the overall plant with developed reddish-purple in the outer leaf portion.
Figure 2:
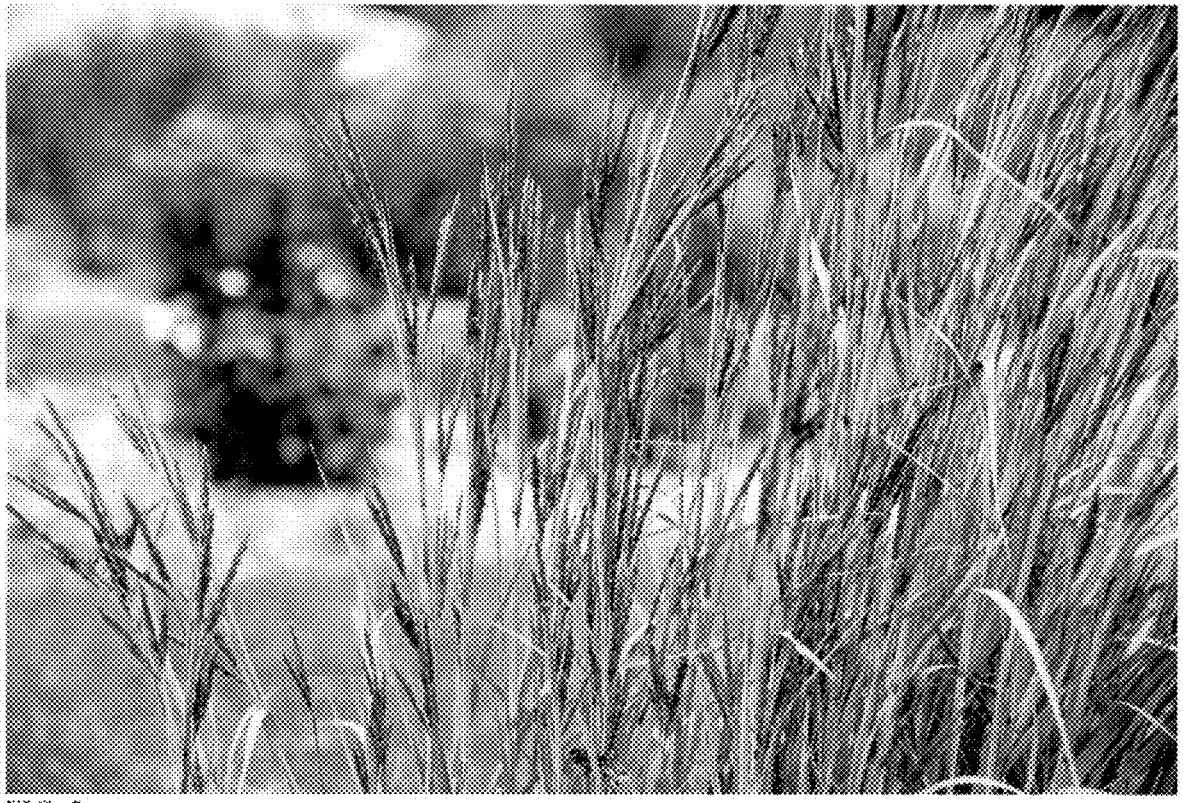
FIG. 2 shows a close-up of the inflorescence in late summer.

The following descriptions and color references are based on the 2015 edition of The Royal Horticultural Society Colour Chart except where common dictionary terms are used. The new plant, 'Blue Steel', has not been observed in all possible environments. The phenotype may vary slightly with different environmental conditions, such as temperature, light, fertility, moisture, and maturity levels, but without any change in the genotype. The following observations and descriptions are of a four-year-old plant in a loamy-sand trial garden of a wholesale perennial nursery in Zeeland, Michigan, USA, grown in full sun with supplemental water and fertilizer as needed.

Parentage: Female or seed parent 20-3-4; male or pollen parent and 20-42-1;

Propagation method: By division of the culms;

Time to finishing in a 3.8-liter pot: Very rapid; about 6 to 8 weeks from 25 mm diameter plug;

Rooting habit: Normal, coarsely branching; root color nearest RHS 155D depending on soil;

Plant description:

Plant shape and habit: Hardy herbaceous perennial forming at tight rhizomatous becoming loose with maturity, with upright culms with arching foliage and greyed-purple inflorescences produced at the top of the clump;

Plant size: Foliage height at flowering time is to about 115 cm tall from the soil line to the top of the foliage and 130 cm tall to the top of flowers; about 118 cm wide at the soil line and about 140 cm at the widest point about 72 cm above the soil;

Rhizome: To about 35 cm long and 3.5 mm diameter; color variable, nearest RHS NN155B proximally and nearest RHS 155C distally between nodes, and nodes nearest RHS N199B; Foliage description: glabrous, glaucous; linear; flat; margin with microscopic marginal dentations; sheathed from the node of attachment to ligule; adaxial and abaxial surfaces dull; strongly arching distally; deciduous but persist through winter;

Foliage size: Blade to about 37 cm long and to about 11 mm wide; sheath to about 19 cm long; average blade about 29 cm long and 9 mm wide, average sheath about 12 cm long, longer at the proximal end; sheath covering about 90% of culm with the distal 2 cm to 4 cm split; typically 7 leaves per culm;

Foliage color: Young adaxial nearest RHS 189B; young abaxial nearest RHS 189B; late summer adaxial distal one-third to two-thirds between RHS 187A and RHS N187B; late summer abaxial distal one-third to two-thirds between RHS N187B and RHS 187A; winter adaxial and abaxial variable, nearest RHS 199D and between RHS 199C and RHS N187C;

Veins: Parallel; midrib about 0.5 mm across; adaxial slightly recessed, abaxial ridged;

Vein color: Adaxial midrib in proximal 5 to 7 cm nearest RHS 192B, abaxial proximal midrib nearest RHS 190A, adaxial and abaxial distal midribs and secondary veins indistinguishable and same color as surrounding leaf;

Ligule: Membranous; with erose margin; to about 1 mm long and about 9 mm across;

Ligule color: Nearest RHS N199B;

Culm: Erect; cylindrical; solid; glabrous; glaucous; dull surface; about 75% enclosed by leaf sheath; about 160 culms per clump;

Culm dimension: To about 130 cm long without panicle, average about 95 cm; to about 5 mm diameter at base; internode length average about 18 cm, shorter proximally;

Culm color: Variable; proximally under sheath nearest RHS 145C; where exposed to high light nearest RHS N187C;

Node description: About 6 per culm before branched inflorescence, slightly swollen to about 7 mm diameter;

Node color: Variable; proximally nearest RHS N148B with and without undertone nearest RHS 187B, distally nearest RHS N187A;

Inflorescence description: Heavily-branched panicle, one panicle per culm; with rame branches;

Flower timing: Beginning late August, flowering into September, panicles dry and remain effective through winter;

No flower fragrance detected;

Panicle: Cylindrical with acute apex; to about 35 cm tall and 6.5 mm across near middle; overall effective color variable, nearest RHS 160A to RHS 147C;

Rachis: Cylindrical; heavily-branched; glabrous, glaucous; to about 36 cm long and about 4 mm diameter at base; about 6 branches to about 28 cm long and about 1.5 mm diameter held at nearly 180-degree above horizontal; color variable, between RHS 4C and RHS 4D where under sheath; nearest RHS 148B where exposed to sun;

Rame: Typically, 3 per branch; to about 6.5 cm long;

Spikelet: Usually with two florets; about 18 mm long; lower floret sessile; upper floret pedicellate;

Rachilla: Thin, terete, stiff; to about 16 mm long and about 0.2 mm diameter; color between RHS 146D and RHS 147D;

Pedicel: Cylindrical; sericeous with hair to about 3 mm long and color nearest RHS NN155D; to about 4 mm long and 0.5 mm diameter; color nearest RHS 183D;

Lower glume: Oblong ovate; apex narrowly acute; base truncate clasping; without awn; to about 8 mm long and 1.5 mm across; color adaxial nearest RHS 187A, abaxial nearest RHS N186B;

Upper glume: Oblong ovate; apex narrowly acute; base truncate; without awn; longitudinally folded; to about 8 mm long and 2 mm across; color adaxial and abaxial between RHS N186C and RHS 187B;

Lemma: Two; oblong ovate; acute apex, truncate base; margin entire;

Outer lemma: Hyaline; about 7 mm long and 1 mm wide; color between RHS 59B and RHS 59C proximally transitioning to nearest RHS NN155D at apex;

Inner lemma: Hyaline; with fine awn about 6 mm long; to about 4 mm long and 0.5 mm across; color nearest RHS 187D;

Gynoecium: Two;

*Stigma*.—Two; plumose; protruding about 2.5 mm from glume; about 3 mm long and about 0.5 mm diameter; color nearest RHS 187A.

*Style*.—Thin; about 1.5 mm long and 0.1 mm diameter; color nearest RHS NN155A.

*Ovary*.—Ellipsoidal; acute apex, rounded base; about 1 mm long and 0.7 mm diameter. color nearest RHS 1C.

Androecium: Two or three;

*Filaments*.—Hair-like; up to 4 mm long and less than 0.1 mm diameter; color nearest RHS NN155D.

*Anthers*.—Two or three; basifixed, longitudinal; about 3 mm long and about 1 mm wide; color initially nearest RHS 11A maturing to nearest RHS 170A.

*Pollen*.—Abundant; very fine; color nearest RHS 11A.

Fruit: Caryopsis; about 7.5 mm long and about 1.5 mm wide; color between RHS 177A and RHS 199B;

Hardiness: At least from USDA zone 4 through 9;

Growth: The new plant is very drought tolerant once established and the stems are resistant to lodging;

Disease and pest resistance or susceptibility: 'Blue Steel' has shown rust (*Puccinia* sp.) resistance compared to other *Andropogon*. Other disease resistance or susceptibility beyond that typical of other Big Bluestem Grasses has not been observed.

I claim:

1. A new and distinct cultivar of ornamental Big Bluestem Grass *Andropogon* plant named 'Blue Steel' as herein described and illustrated.

* * * * *